US00PP08355P

United States Patent [19]

Tracy, Sr.

[11] Patent Number: Plant 8,355

[45] Date of Patent: Aug. 31, 1993

[54] HYBRID TEA ROSE PLANT NAMED HILCOT

[75] Inventor: Daniel L. Tracy, Sr., Richmond, Ind.

[73] Assignee: E. G. Hill Comapny, Inc., Richmond, Ind.

[21] Appl. No.: 919,720

[22] Filed: Jul. 24, 1992

[51] Int. Cl.[5] ..... A01H 5/00

[52] U.S. Cl. ..... Plt./16

[58] Field of Search ..... Plt. 16, 11, 15, 17

[56] References Cited

U.S. PATENT DOCUMENTS

PP. 4,868 7/1992 Meilland ..... PLT. 15

*Primary Examiner*—Howard J. Locker

*Attorney, Agent, or Firm*—Christie, Parker & Hale

[57] ABSTRACT

A new variety of hybrid tea rose having peach flowers produced on a plant suitable for greenhouse growing.

2 Drawing Sheets

SUMMARY OF THE INVENTION

The present invention relates to a new and distinct variety of rose plant of the hybrid tea rose class, which was originated by my crossing as the seed parent the variety meirilocra known as 'Capella', U.S. Plant Pat. No. 4,868, and as the pollen parent the variety known as 'Golden Fantasie', U.S. Plant Pat. No. 3,272. The varietal denomination of this new rose is 'Hilcot'.

Among the novel characteristics possessed by this new variety which distinguishes it from its parents and all other varieties of which I am aware are its attractive flowers having unusual opening coloration. At the cut flower stage the blooms appear as an orange blend. However, suggestions of peach tones appear when the bloom is about one-half open. At the open bloom stage the color tends to be seen as a yellow blend. The flowers are large and are borne singly in a manner typical of hybrid tea varieties and the plant produces strong, upright canes with rich, green foliage.

Asexual reproduction by propagation by grafting of the new variety as performed in Richmond, Ind. shows that the foregoing and other distinguishing characteristics come true to form and are established and transmitted through succeeding propagations. The new variety can be asexually propagated by budding, grafting, propagation from cuttings and micropropagation.

BRIEF DESCRIPTION OF ILLUSTRATION

The accompanying illustrations show typical specimens of the flowers and vegetative growth of the new variety depicted in color as nearly true as it is reasonably possible to make the same in a color illustration of this character. Phenotypic expression, including colors, may vary depending upon growing conditions, such as climate, soil, and cultivation conditions.

One of the accompanying illustrations shows plant parts, including compound three and five leaflets leans, a stem, new growth, buds after sepals part and after sepals fall, a bloom ⅓ open and a bloom fully open. The other illustration depicts typical form and configuration of flower and bud as cut flowers.

DETAILED DESCRIPTION OF THE NEW VARIETY

The following is a detailed description of my new variety, with color terminology in accordance with The Royal Horticultural Society Colour Chart (R.H.S.C.C.). The terminology used in the color descriptions herein refers to plate numbers in the aforementioned color chart.

Parentage: Seedling

*Seed parent.*—Meirilocra (also known as Capella).

*Pollen parent.*—'Golden Fantasie'.

Class: Hybrid tea.

The following further horticultural observations were made of specimens grown in a greenhouse in Richmond, Ind. in the months of November–February.

FLOWER

Blooming habit: Nearly continuous.

A. Bud:

(1) *Size.*—Medium.

(2) *Form.*—Ovoid becoming urn-shaped as sepals fall.

(3) *Color.*—When sepals first divide, near 37A.

(4) *Sepals.*—Funnel shape, hooded over bud, curl back when flowers open, usually 5 in number; inside color near 138C; outside color near 143C.

(5) *Peduncle.*—Length — about 4 inches. Aspect — smooth. Strength — heavy and erect. Color — near 143B.

B. Bracts:

*Size.*—Small leaf-like with serrate edges; usually one and sometimes two.

*Form.*—elliptical

*Location in relation to flower.*—Usually about 2 inches below base of flower.

C. Bloom:

(1) *Size.*—Very large — about 5½ to 6 inches.

(2) *Borne.*—Singly, one to a stem.

(3) *Form.*—High-centered, urn-shaped at first; at maturity, high centers and imbricated, attractive open bloom, some outer petals quill to points, inner petals roll under loosely.

(4) *Petalage.*—Number of petals under normal conditions — about 26–30.

(5) *Color.*—After sepals fall and petals unfurl, outer petals top surface, near 24A, petal undersurface, near 31A. As flower opens, inner petals top surface near 15C and inner petals undersurface near 24C. Color at point of petal attachment is near 9B. As blooms age, when bloom is ⅓ to ½ open color is orange blend with peach tones. When fully open, color is a yellow blend with petal top surface near 19C and petal undersurface near 20C. General tonality at a distance is orange blend to cream peach.

D. Petals:
(1) *Texture.*—Leathery.
(2) *Appearance.*—Satiny.
(3) *Form.*—Short, fan shaped.
(4) *Arrangement.*—Normal and imbricated.
(5) *Petaloids in center.*—Few.
(6) *Persistence.*—Drop off cleanly in greenhouse.
(7) *Fragrance.*—Strong.
(8) *Lasting quality.*—About 8days on plant and about 6 to 7 days after cutting.

REPRODUCTIVE ORGANS

A. Stamens, filaments and anthers:
*Arrangement and color.*—Arranged around styles. Color— filaments near 13B, anthers near 13B.

B. Pollen:
*Color.*—near 162C.

C. Styles: Uneven lengths.

D. Stigmas: Near 11A.

E. Hips:
*Shape.*—Pear shaped.
*Size.*—Large, a few seeds protrude but most are encased in hip.

PLANT

A. Form: Bushy, upright.

B. Growth: Vigorous and upright.
*Height attained first season.*—About 24 to 26 inches.

C. Foliage: Usually compound 3 and 5 leaflets.
(1) *Size.*—Large — about 6 inches.
(2) *Quantity.*—Abundant.

(3) *Color.*—New foliage: Upper side — near 139A. Underside — near 139C. Old foliage: Upper side — near 137A. Underside — near 138B.
(4) *Shape.*—Acuminate.
(5) *Texture*—Upper side is leathery; Underside is smooth.
(6) *Edge.*—Serrate.
(7) *Serration.*—Saw-toothed, pointing forwards.
(8) *Leaf stem.*—Color — medium green.
(9) *Stipules.*—Narrow, generally triangular with comb shape edges.
(10) *Auricle.*—Short, pointing upward.
(11) *Rachis.*—Upperside is grooved and smooth. Underside usually has one to two thorns.
(12) *Resistance to Disease.*—Slight susceptibility to powdery mildew.

D. Wood:
(1) *New wood.*—Color — near 47B. Bark — smooth.
(2) *Old wood.*—Color— near 144A. Bark — smooth.
(3) *Flower stem.*—Length from last cut — 22 to 26 inches.

E. Thorns:
*Quantity (main stalk).*—Ordinary.
*On laterals from stalk.*—Few.
*Form.*—Thin, downward angle.
*Length.*—Medium to large.
*Color.*—Near 53A.
*Position.*—Irregular.
*Prickles.*—None.

I claim:

1. A new and distinct variety of rose plant of the hybrid tea rose class, substantially as shown and described.

* * * * *

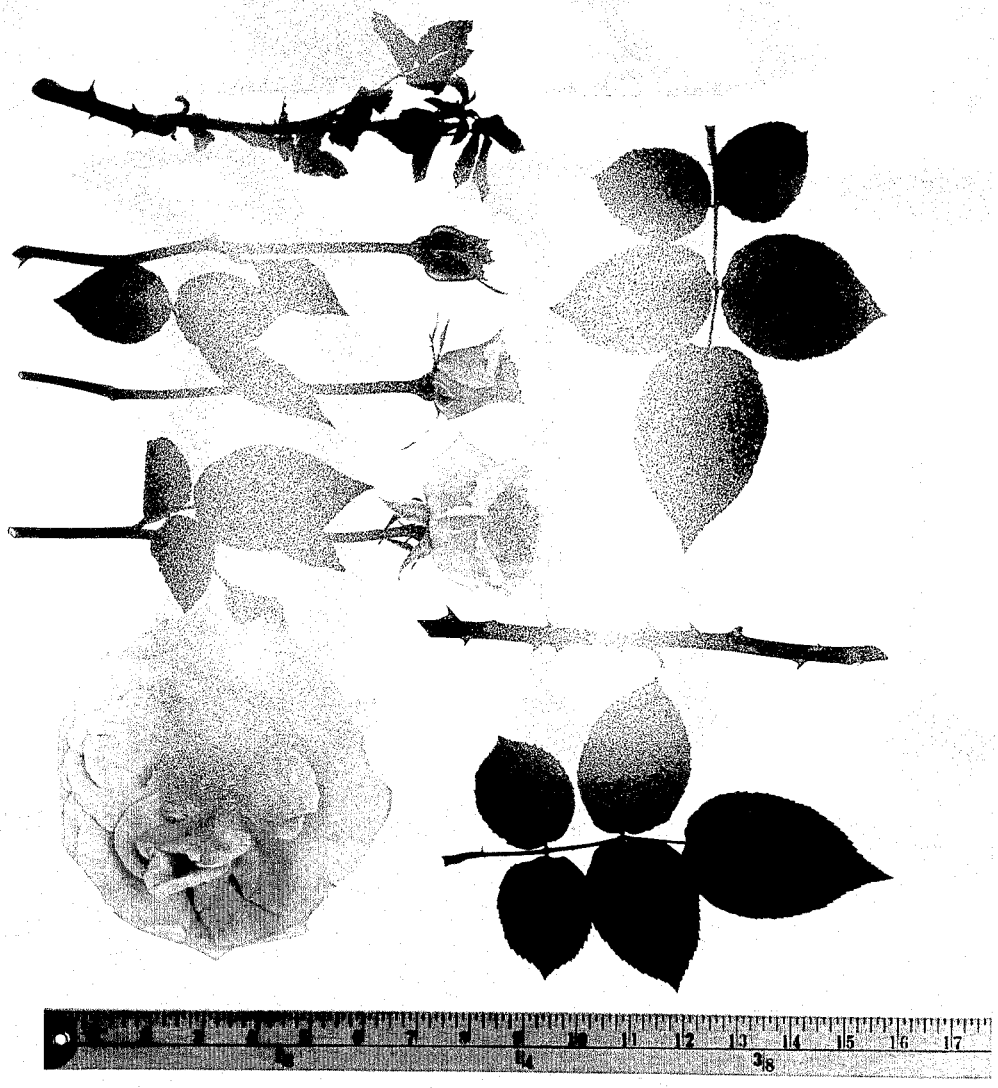

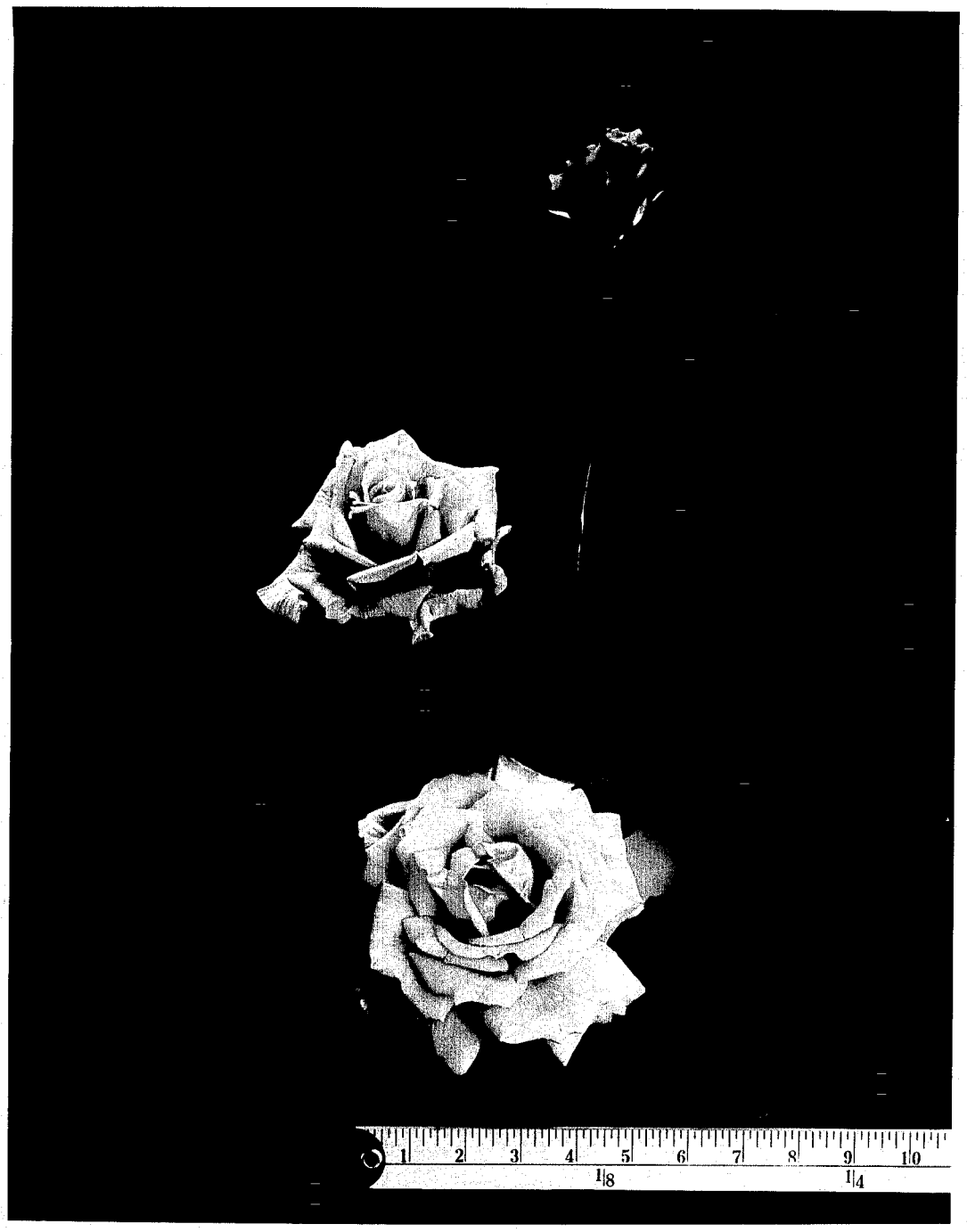
1
2
3
4
5
6
7
8
9
10
1/8
1/4

UNITED STATES PATENT AND TRADEMARK OFFICE

CERTIFICATE OF CORRECTION

PATENT NO. : Plant 8,355

DATED : August 31, 1993

INVENTOR(S) : Daniel L. Tracy, Sr.

It is certified that error appears in the above-indentified patent and that said Letters Patent is hereby corrected as shown below:

Column 1, line 6, change "meiriloca known" to -- 'Meiriloca', also known --.

Column 1, line 37, change "leans" to -- leaves --.

Column 3, line 14, change "8days" to -- 8 days --.

Signed and Sealed this

Seventh Day of June, 1994

Bruce Lehman

*Attest:*

BRUCE LEHMAN

*Attesting Officer*

*Commissioner of Patents and Trademarks*